(12) United States Patent (10) Patent No.: US 12,045,929 B2
Dascal et al. (45) Date of Patent: Jul. 23, 2024

(54) SYSTEM AND METHOD FOR GENERATING THREE DIMENSIONAL GEOMETRIC MODELS OF ANATOMICAL REGIONS

(71) Applicant: ST. JUDE MEDICAL, CARDIOLOGY DIVISION, INC., St. Paul, MN (US)

(72) Inventors: Lorina Dascal, Haifa (IL); Oded Sudarsky, Kfar Yedidya (IL); Jacob Segev, Haifa (IL); Alexander Dathskovsky, Kiryat Bialik (IL); Yaron Valach, Atlit (IL); Maxim Yoresh, Haifa (IL)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 60 days.

(21) Appl. No.: 17/793,077

(22) PCT Filed: Jan. 14, 2021

(86) PCT No.: PCT/US2021/013440
§ 371 (c)(1),
(2) Date: Jul. 15, 2022

(87) PCT Pub. No.: WO2021/150421
PCT Pub. Date: Jul. 29, 2021

(65) Prior Publication Data
US 2023/0039065 A1    Feb. 9, 2023

Related U.S. Application Data

(60) Provisional application No. 62/965,566, filed on Jan. 24, 2020.

(51) Int. Cl.
*G06T 15/08*     (2011.01)
*G06T 19/20*     (2011.01)

(52) U.S. Cl.
CPC .............. *G06T 15/08* (2013.01); *G06T 19/20* (2013.01); *G06T 2210/41* (2013.01)

(58) Field of Classification Search
None
See application file for complete search history.

(56) References Cited

U.S. PATENT DOCUMENTS 5,697,377 A    11/1997  Wittkampf
5,983,126 A    11/1999  Wittkampf
(Continued)

OTHER PUBLICATIONS

Aditya B Koolwal et al. "A Fast Slam Approach to Freehand 3-D Ultrasound Reconstruction for Catheter Ablation Guidance in the Left Atrium", Ultrasound in Medicine and Biology, New York, NY, US, vol. 37, No. 12, Aug. 9, 2011, pp. 2037-2054.
(Continued)

*Primary Examiner* — Yingchun He
(74) *Attorney, Agent, or Firm* — Wiley Rein LLP

(57) ABSTRACT

A three-dimensional geometric image of an anatomical region is generated from a plurality of two-dimensional echographic image slices of the region. The image slices are filtered using a reaction-diffusion partial differential equation model before being arranged into a voxel space. Each voxel is then assigned a voxel value to create a volumetric data set from which the volumetric image can be rendered. The image is rendered from far to near, relative to a preset viewing direction, by an alpha-blending process. The alpha value at any given voxel can be determined using the magnitude of the density gradient vector at that voxel. Similarly, the direction of the density gradient vector at a given voxel can be used as a surface normal vector for shading purposes at that voxel.

16 Claims, 7 Drawing Sheets

(56) References Cited

U.S. PATENT DOCUMENTS

| | | | |
|---|---|---|---|
| 6,640,119 B1 | 10/2003 | Beatty et al. | |
| 6,728,562 B1 | 4/2004 | Budd et al. | |
| 6,939,309 B1 | 9/2005 | Beatty et al. | |
| 6,947,785 B1 | 9/2005 | Beatty et al. | |
| 6,978,168 B2 | 12/2005 | Beatty et al. | |
| 6,990,370 B1 | 1/2006 | Beatty et al. | |
| 2005/0043619 A1* | 2/2005 | Sumanaweera | G06T 15/08 600/437 |
| 2006/0241445 A1 | 10/2006 | Altmann et al. | |
| 2012/0165664 A1 | 6/2012 | Hill et al. | |
| 2014/0022252 A1* | 1/2014 | Watanabe | G06T 15/005 345/426 |
| 2014/0306952 A1* | 10/2014 | Oka | G06T 15/10 345/419 |
| 2015/0310632 A1* | 10/2015 | Banerjee | G06F 18/24 382/131 |
| 2019/0333189 A1* | 10/2019 | Tamal | G06T 5/002 |

OTHER PUBLICATIONS

Antonio Malvasi et al: A three-dimensional morphological reconstruction of uterine leiomyoma pseudocapsule vasculature by the Allen-Cahn mathematical model, Biomedicine and Pharmacotherapy, Elsevier, FR, vol. 65, No. 5, Apr. 7, 2011, pp. 359-363.

Shigeru Muraki et al: "A survey of medical applications of 3D image analysis and computer graphics", Systems & Computers in Japan., vol. 37, No. 1, Jan. 1, 2005, pp. 13-46.

Jonker P.P. et al: "A scalable real-time image processing pipeline", Pattern Recognition, 1992, vol. IV. Conference D: Architectures for Vision and Pattern Recognition, Proceedings., 11th IAPR International Conference on the Hague, Netherlands Aug. 30-Sep. 3, 1992, vol. 8, Jan. 1, 1995, pp. 142-146.

International Search Report and Written Opinion for PCT/US2021/013440 dated Jul. 12, 2021.

\* cited by examiner

SYSTEM AND METHOD FOR GENERATING THREE DIMENSIONAL GEOMETRIC MODELS OF ANATOMICAL REGIONS

CROSS-REFERENCE TO RELATED APPLICATIONS

This application claims the benefit of U.S. provisional application No. 62/965,566, filed 24 Jan. 2020, which is hereby incorporated by reference in its entirety as though fully set forth herein.

BACKGROUND

The instant disclosure relates to imaging, including medical imaging. In particular, the instant disclosure relates to apparatuses, systems, and methods for generating three-dimensional geometric images of anatomical regions.

Ultrasound transducers are utilized in a variety of medical applications. In many applications, the transducer is mounted in a catheter that can be navigated through a patient's vasculature and/or body organs to a site of interest.

One such application is intracardiac echocardiography ("ICE"), which utilizes ultrasound to generate a three-dimensional volumetric image of a subject's heart from a plurality of two-dimensional ultrasound images. For instance, United States patent application publication no. 2006/0241445 teaches a method for modeling an anatomical structure from a plurality of two-dimensional ultrasound images.

There are, however, certain challenges attendant the creation of such volumetric images, such as unsharp and vague boundaries, variations in topology, speckle phenomenon, and attenuation.

BRIEF SUMMARY

Disclosed herein is a method of generating a three-dimensional geometric image of an anatomical region, including the steps of: defining a three-dimensional voxel space including a plurality of voxels; receiving a plurality of two-dimensional echographic image slices of the anatomical region, wherein each image slice of the plurality of image slices is associated with localization information; filtering the plurality of image slices using a reaction-diffusion partial differential equation model; arranging the filtered plurality of image slices into the voxel space using the associated localization information; assigning each voxel of the plurality of voxels a voxel value using the arranged, filtered plurality of image slices, thereby creating a volumetric data set; and rendering a three-dimensional volumetric image from the three-dimensional data set.

In aspects of the disclosure, the step of assigning each voxel of the plurality of voxels a voxel value using the arranged, filtered plurality of image slices can include: assigning each voxel of the plurality of voxels a greyscale value; defining a neighborhood size; and, for each voxel within the plurality of voxels: assigning the voxel a greyscale array, wherein the greyscale array is defined by the respective greyscale values of a neighborhood of the plurality of voxels within the neighborhood size of the voxel; quantizing the greyscale array to a preset number of buckets; and assigning the voxel value to the voxel according to the quantized greyscale array. For example, the voxel value can be assigned according to a majority vote of the quantized voxel array.

According to embodiments, the step of filtering the plurality of image slices using a reaction-diffusion partial differential equation model includes filtering the plurality of image slices using an Allen-Cahn-type reaction-diffusion model.

It is contemplated that the step of rendering a three-dimensional volumetric image from the three-dimensional data set includes: dividing the voxel space into a plurality of slices perpendicular to a preset viewing direction; and alpha-blending the plurality of slices.

The step of dividing the voxel space into a plurality of slices perpendicular to a preset viewing direction can occur from a most distant slice of the plurality of slices to a nearest slice of the plurality of slices, as determined relative to the preset viewing direction. Depth cueing can be achieved by assigning each slice a color that varies gradually from the most distant slice to the least distant slice relative to the preset viewing direction. It is also contemplated that depth cueing colors may only be varied between slices containing voxel values within a range of interest. Indeed, rendering may be accelerated by processing only slices that contain voxel values within the range of interest; slices that contain voxel values within the range of interest can be determined quickly using graphics hardware capabilities such as OpenGL shaders.

In aspects of the disclosure, the step of alpha-blending the plurality of slices includes, for each voxel within the plurality of voxels: computing a density gradient vector; computing a magnitude of the density gradient vector; and assigning an alpha value using the magnitude of the density gradient vector. For instance, the magnitude of the density gradient vector can be normalized, and then the normalized magnitude of the density gradient vector can be exponentiated by an opacity bias, which can be user preset and/or scaled. The magnitude of the density gradient vector can also be calculated quickly using graphics hardware capabilities, such as OpenGL shaders.

It is also contemplated that the step of rendering the three-dimensional volumetric image from the three-dimensional data set further includes, for each voxel within the plurality of voxels: computing a density gradient vector; computing a direction of the density gradient vector; and defining the direction of the density gradient vector as a surface normal vector for shading purposes.

Also disclosed herein is a method of generating a three-dimensional geometric image of an anatomical region, including the steps of: defining a three-dimensional voxel space including a plurality of voxels; receiving a plurality of two-dimensional echographic image slices of the anatomical region, wherein each image slice of the plurality of image slices is associated with localization information; arranging the plurality of image slices into the voxel space using the associated localization information, thereby creating a volumetric data set; and rendering a three-dimensional volumetric image from the three-dimensional data set, wherein rendering the three-dimensional volumetric image from the three-dimensional data set includes, for each voxel within the plurality of voxels: computing a density gradient vector; computing a magnitude of the density gradient vector; and assigning an alpha value for alpha-blending purposes using the magnitude of the density gradient vector.

The alpha value can be assigned by normalizing the magnitude of the density gradient vector; and exponentiating the normalized magnitude of the density gradient vector by an opacity bias. The opacity bias can be a user preset value and/or a scaled value (that is, a scaled opacity bias).

The step of rendering the three-dimensional volumetric image from the three-dimensional data set can also include computing a direction of the density gradient vector; and defining the direction of the density gradient vector as a surface normal vector for shading purposes. The direction of the density gradient vector can also be calculated quickly using graphics hardware capabilities, such as OpenGL shaders.

In embodiments of the disclosure, the method also includes, prior to arranging the plurality of image slices into the voxel space using the associated localization information, thereby creating the volumetric data set, filtering the plurality of image slices using a reaction-diffusion partial differential equation model, such as an Allen-Cahn-type reaction-diffusion model.

It is contemplated that the step of arranging the plurality of image slices into the voxel space using the associated localization information, thereby creating the volumetric data set, includes, for each voxel of the plurality of voxels: assigning the voxel a greyscale value; defining a neighborhood size; assigning the voxel a greyscale array, wherein the greyscale array is defined by the respective greyscale values of a neighborhood of the plurality of voxels within the neighborhood size of the voxel; quantizing the greyscale array to a preset number of buckets; and assigning a final voxel value to the voxel according to the quantized greyscale array.

The instant disclosure also provides a system for generating a three-dimensional geometric image of an anatomical region, including an imaging and modeling module. The imaging and modeling module can be configured to: define a three-dimensional voxel space including a plurality of voxels; receive a plurality of two-dimensional echographic image slices of the anatomical region, wherein each image slice of the plurality of image slices is associated with localization information; arrange the plurality of image slices into the voxel space using the associated localization information, thereby creating a volumetric data set; compute a density gradient vector for each voxel within the plurality of voxels; and render a three-dimensional volumetric image from the three-dimensional data set using a magnitude of the density gradient vector to assign an alpha value for alpha-blending purposes and a direction of the density gradient vector as a surface normal vector for shading purposes.

The foregoing and other aspects, features, details, utilities, and advantages of the present invention will be apparent from reading the following description and claims, and from reviewing the accompanying drawings.

While multiple embodiments are disclosed, still other embodiments of the present disclosure will become apparent to those skilled in the art from the following detailed description, which shows and describes illustrative embodiments. Accordingly, the drawings and detailed description are to be regarded as illustrative in nature and not restrictive.

DETAILED DESCRIPTION

The instant disclosure provides systems, apparatuses, and methods for the creation of three-dimensional geometric images of anatomical regions. For purposes of illustration, aspects of the disclosure will be described in detail herein with reference to the creation of a three-dimensional geometric image of a patient's heart via intracardiac echocardiography ("ICE"). It is contemplated, however, that the apparatuses, systems, and methods described herein can be used in other contexts.

Figure 1:
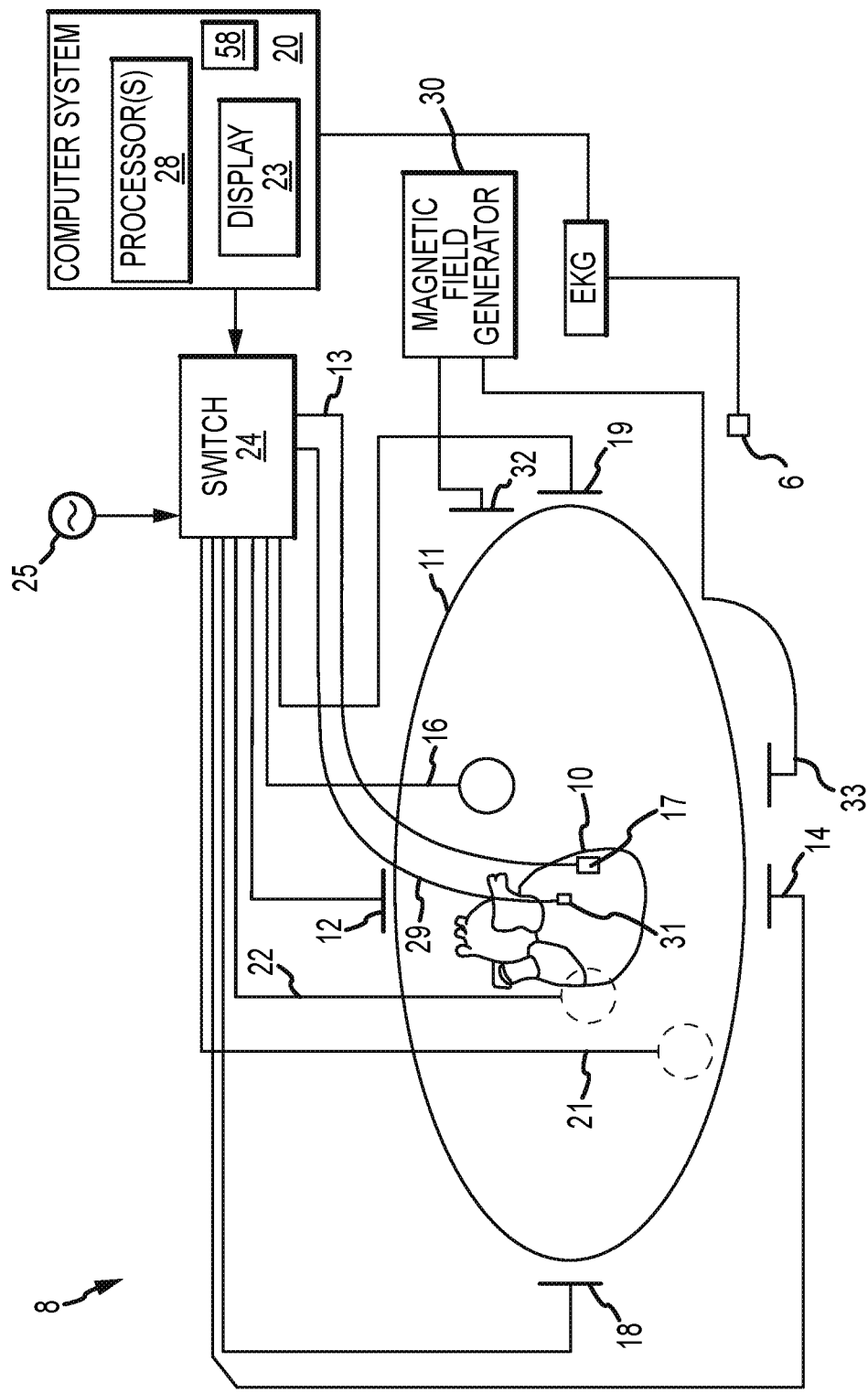
FIG. 1 schematically depicts a system for generating a three-dimensional geometric image of an anatomical region according to aspects of the instant disclosure.

FIG. 1 is a schematic diagram of an exemplary system 8 for generating a three-dimensional geometric image of, for example, a patient's heart. As one of ordinary skill in the art will recognize, and as will be further described below, system 8 determines the location, and in some aspects the orientation, of objects, typically within a three-dimensional space, and expresses those locations as position information determined relative to at least one reference.

As depicted in FIG. 1 and described herein, system 8 can be a hybrid system that incorporates both impedance-based and magnetic-based localization capabilities. In some embodiments, system 8 is the EnSite Precision™ cardiac mapping system of Abbott Laboratories (Abbott Park, Illinois). Other localization systems, however, may be used in connection with the present teachings, including for example the RHYTHMIA HDX™ mapping system of Boston Scientific Corporation (Marlborough, Massachusetts), the CARTO navigation and location system of Biosense Webster, Inc. (Irvine, California), the AURORA® system of Northern Digital Inc. (Waterloo, Ontario), and Stereotaxis, Inc.'s (St. Louis, Missouri) NIOBE® Magnetic Navigation System.

The localization and mapping systems described in the following patents (all of which are hereby incorporated by reference in their entireties) can also be used with the present invention: U.S. Pat. Nos. 6,990,370; 6,978,168; 6,947,785; 6,939,309; 6,728,562; 6,640,119; 5,983,126; and 5,697,377.

The foregoing systems, and the modalities they employ to localize a medical device, will be familiar to those of ordinary skill in the art. Insofar as the ordinarily skilled artisan will appreciate the basic operation of such systems, they are only described herein to the extent necessary to understand the instant disclosure.

For simplicity of illustration, the patient 11 is depicted schematically as an oval. In the embodiment shown in FIG. 1, three sets of surface electrodes (e.g., patch electrodes 12, 14, 16, 18, 19, and 22) are shown coupled to a current source 25. Patch electrodes 12, 14, 16, 18, 19, and 22 define three generally orthogonal axes, referred to herein as an x-axis, a y-axis, and a z-axis. The patient's heart 10 lies within the field generated by patch electrodes 12, 14, 16, 18, 19, and 22.

FIG. 1 also depicts a magnetic source 30, which is coupled to magnetic field generators. In the interest of clarity, only two magnetic field generators 32 and 33 are depicted in FIG. 1, but it should be understood that additional magnetic field generators (e.g., a total of six magnetic field generators, defining three generally orthogonal axes analogous to those defined by patch electrodes 12, 14, 16, 18, 19, and 22) can be used without departing from the scope of the present teachings.

Patient 11 may also have most or all of the conventional electrocardiogram ("ECG" or "EKG") system leads in place. In certain embodiments, for example, a standard set of 12 ECG leads may be utilized for sensing electrocardiograms on the patient's heart 10. This ECG information is available to the system 8 (e.g., it can be provided as input to computer system 20). Insofar as ECG leads are well understood, and for the sake of clarity of illustration, only a single lead 6 and its connection to computer 20 is shown in FIG. 1.

An ultrasound imaging catheter 13 is also shown schematically in FIG. 1. In aspects of the disclosure, catheter 13 can be an ultrasonic echocardiography (ICE) catheter similar to Abbott Laboratories' ViewFlex™ Xtra ICE catheter. Catheter 13 further includes a sensor 17 to sense the magnetic fields generated by magnetic field generators 32 and 33. As those of ordinary skill in the art will appreciate, catheter 13 can also include one or more electrodes to sense the electrical fields generated by patch electrodes 12, 14, 16, 18, 19, and 22.

Returning now to FIG. 1, in some embodiments, a fixed reference 31 (e.g., attached to a wall of the heart 10) is shown on a second catheter 29. Often, reference 31 is placed in the coronary sinus and defines the origin of a coordinate system with reference to which catheter 13 is localized by system 8.

Computer 20 may comprise, for example, a conventional general-purpose computer, a special-purpose computer, a distributed computer, or any other type of computer. The computer 20 may comprise one or more processors 28, such as a single central processing unit ("CPU"), or a plurality of processing units, commonly referred to as a parallel processing environment, which may execute instructions to practice the various aspects described herein.

Amongst other things, computer system 8 can interpret measurements by sensor 17 of the magnetic and/or electrical fields generated by magnetic field generators 32, 33 and patch electrodes 12, 14, 16, 18, 19, and 22 respectively, to determine the position and orientation of catheter 13 within heart 10. The term "localization" is used herein to describe the determination of the position and orientation of an object, such as catheter 13, within such fields.

Aspects of the disclosure relate to the creation of three-dimensional images of cardiac geometry from echographic imagery captured, for example, by catheter 13. Accordingly, system 8 can also include an imaging and modeling module 58.

Figure 2:
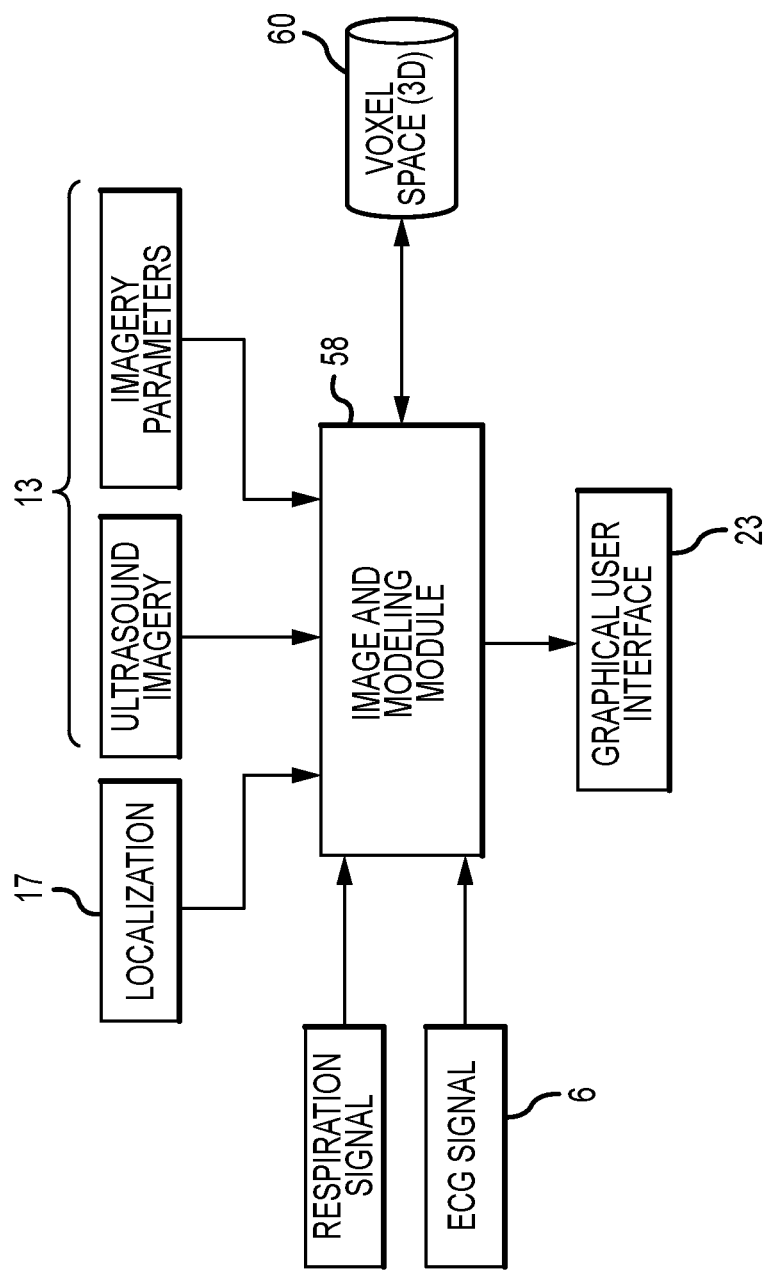
FIG. 2 is a block diagram showing inputs and outputs from an imaging and modeling module as disclosed herein.

FIG. 2 is a block diagram of imaging and modeling module 58 and its inputs and outputs according to aspects disclosed herein. As discussed in detail below, imaging and modeling module 58 can synthesize localization data (e.g., of sensor 17 carried by catheter 13) with ultrasound imagery parameters and data (e.g., from catheter 13) into a three-dimensional voxel space 60 that can be graphically output (e.g., on display 23). Imaging and modeling module 58 can optionally synthesize ECG and/or respiration data, for example to gate the collection of localization and imagery information. Those of ordinary skill in the art will appreciate, however, that the teachings herein can advantageously be applied without gating the collection of localization and imagery information to the cardiac and/or respiratory cycles.

Figure 3:
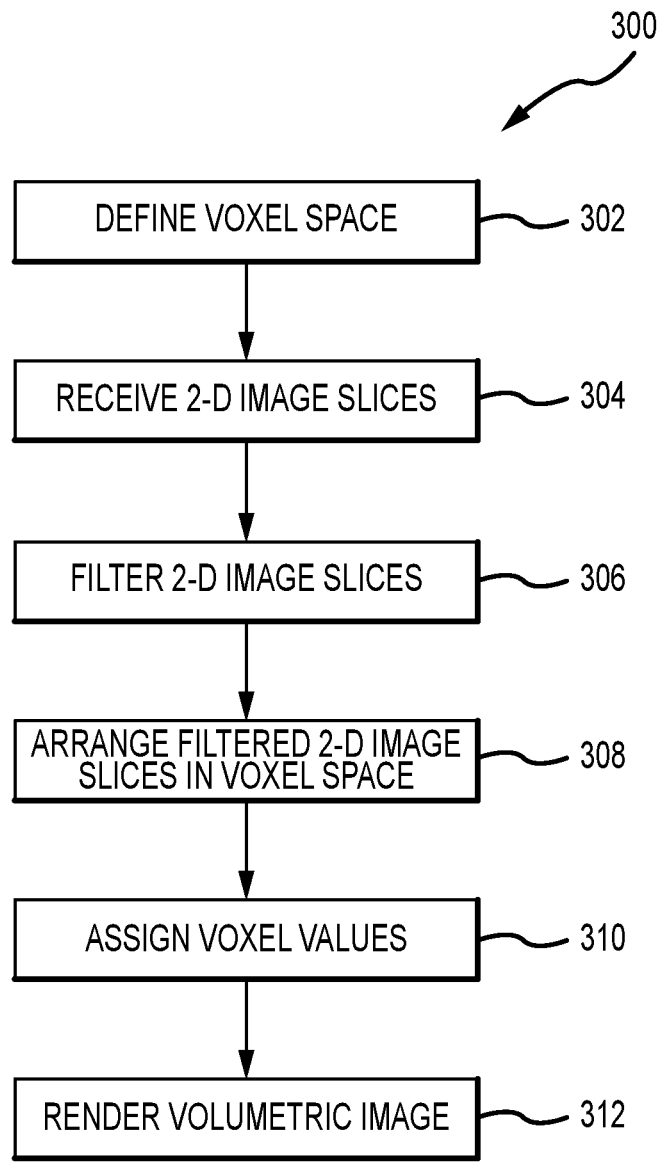
FIG. 3 is a flowchart of representative steps that can be followed when creating a three-dimensional volumetric image according to exemplary embodiments disclosed herein.

One exemplary method of generating a three-dimensional geometric image according to the present teachings will be explained with reference to the flowchart 300 of representative steps presented as FIG. 3. In some embodiments, for example, flowchart 300 may represent several exemplary steps that can be carried out by system 8 of FIG. 1 (e.g., by processor 28 and/or imaging and modeling module 58). It should be understood that the representative steps described below can be either hardware- and/or software-implemented.

In block 302, system 8 defines a three-dimensional voxel space including a plurality of voxels. This voxel space provides an environment within which to visualize the three-dimensional geometric image generated by system 8.

In block 304, system 8 receives a plurality of two-dimensional image slices of the heart from ICE catheter 13. Those of ordinary skill in the art will be familiar with echographic imaging modalities, such as B-mode ultrasound and color Doppler echocardiography, that are suitable for use in acquiring the image slices in block 304.

Because, in some embodiments, catheter 13 incorporates sensor 17, each two-dimensional image slice can also be associated with localization information. That is, each image slice can be associated with a particular position and orientation of catheter 13. In turn, and as further described below, system 8 (e.g., module 58) can assemble the plurality of two-dimensional image slices into a three-dimensional geometric image.

In block 306, system 8 filters the image slices received in block 304. In aspects of the disclosure, a reaction-diffusion partial differential equation model, such as an Allen-Cahn-type reaction-diffusion model, can be used to filter the image slices.

Figure 4B:
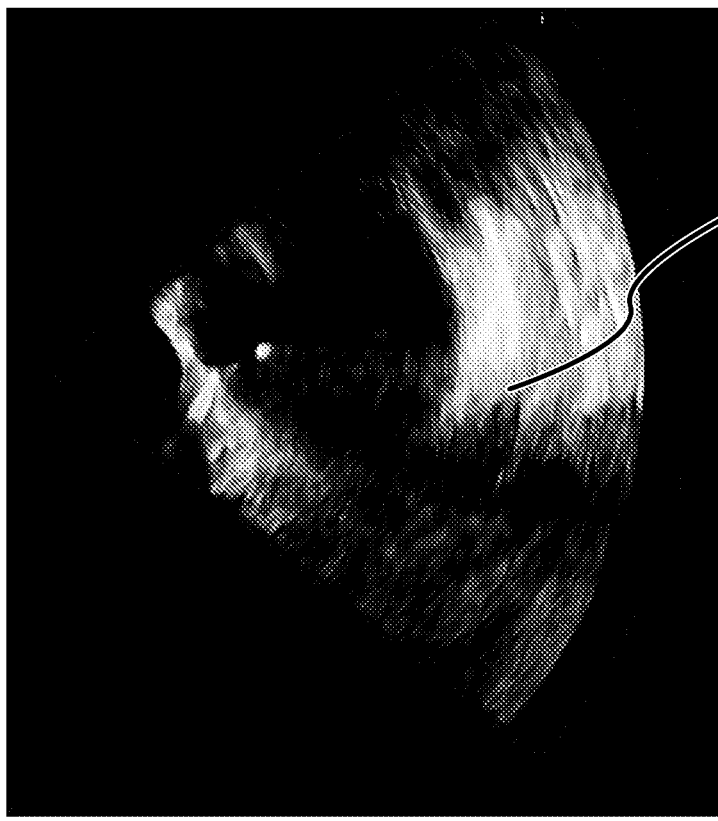
FIG. 4B depicts the same image slice after such filtering.
Figure 4A:
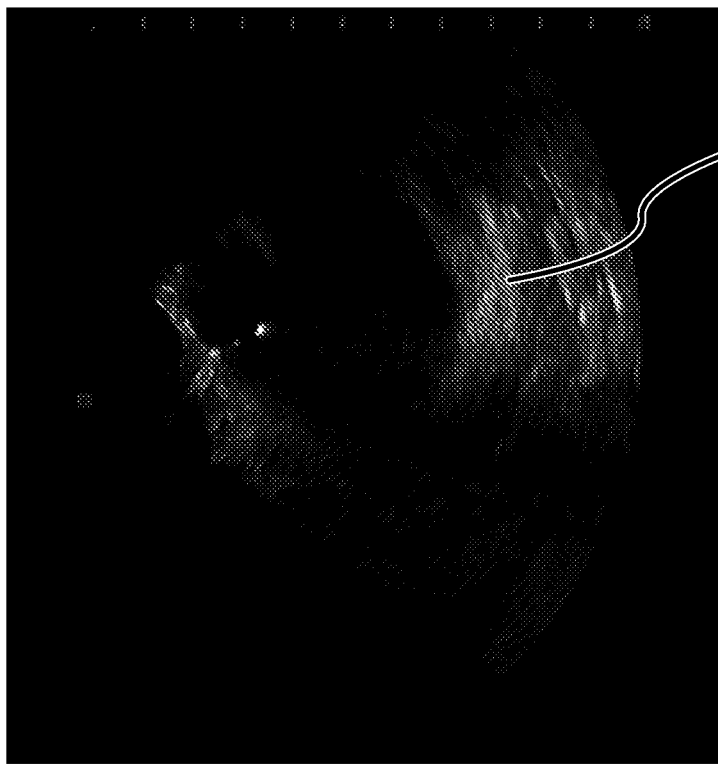
FIG. 4A depicts a two-dimensional image slice prior to filtering according to aspects of the instant disclosure.

The use of an Allen-Cahn-type model smooths the respective images, enhances the tissue contrast (e.g., between tissue and blood pool), and preserves the main features of the images. These qualities can be seen, for example, in the comparison between FIG. 4A, which is an initial two-dimensional image slice 400, and FIG. 4B, which is the image slice after filtering using an Allen-Cahn-type model 402.

For instance, initial two-dimensional image slice 400 can be evolved using an equation $u_t = |curv(u)|^{1/3} |Du| + \alpha f(u)$, where the reaction term $f(u) = u(1-u)^2$ and $\alpha$ retrieves the weighting between diffusion and reaction.

The diffusion term $Diff = |curv(u)|^{1/3} |Du|$ is well-suited for shape recognition due to its affine invariant property. It is contemplated, however, that other diffusion models can be used to equally good advantage.

The definition of $curv(u)$, in turn, can be based on the links between the curvature vector of a level line of u and $curv(u)$, as follows:

$$curv(u)(x) = \frac{u_y^2 u_{xx} - 2u_x u_y u_{xy} + u_x^2 u_{yy}}{(u_x^2 + u_y^2)^{3/2}}.$$

Thus, according to aspects of the disclosure, the reaction-diffusion equation can also be expressed as follows: $u_t = (u_y^2 u_{xx} - 2u_x u_y u_{xy} + u_x^2 u_{yy})^{1/3} + \alpha u(1-u^2)$.

It is contemplated that the filtering step (that is, block 306) can be implemented using the CUDA® parallel computing platform (NVIDIA Corporation; Santa Clara, CA).

In block 308, the filtered two-dimensional image slices are arranged in the voxel space according to their respective localization information. In general, techniques for arranging two-dimensional echographic image slices into a three-dimensional voxel space will be familiar to the ordinarily skilled artisan (see, e.g., United States patent application publication no. 2012/0165664, which is hereby incorporated by reference as though fully set forth herein), and such techniques therefore need not be discussed in further detail herein.

Figure 5:
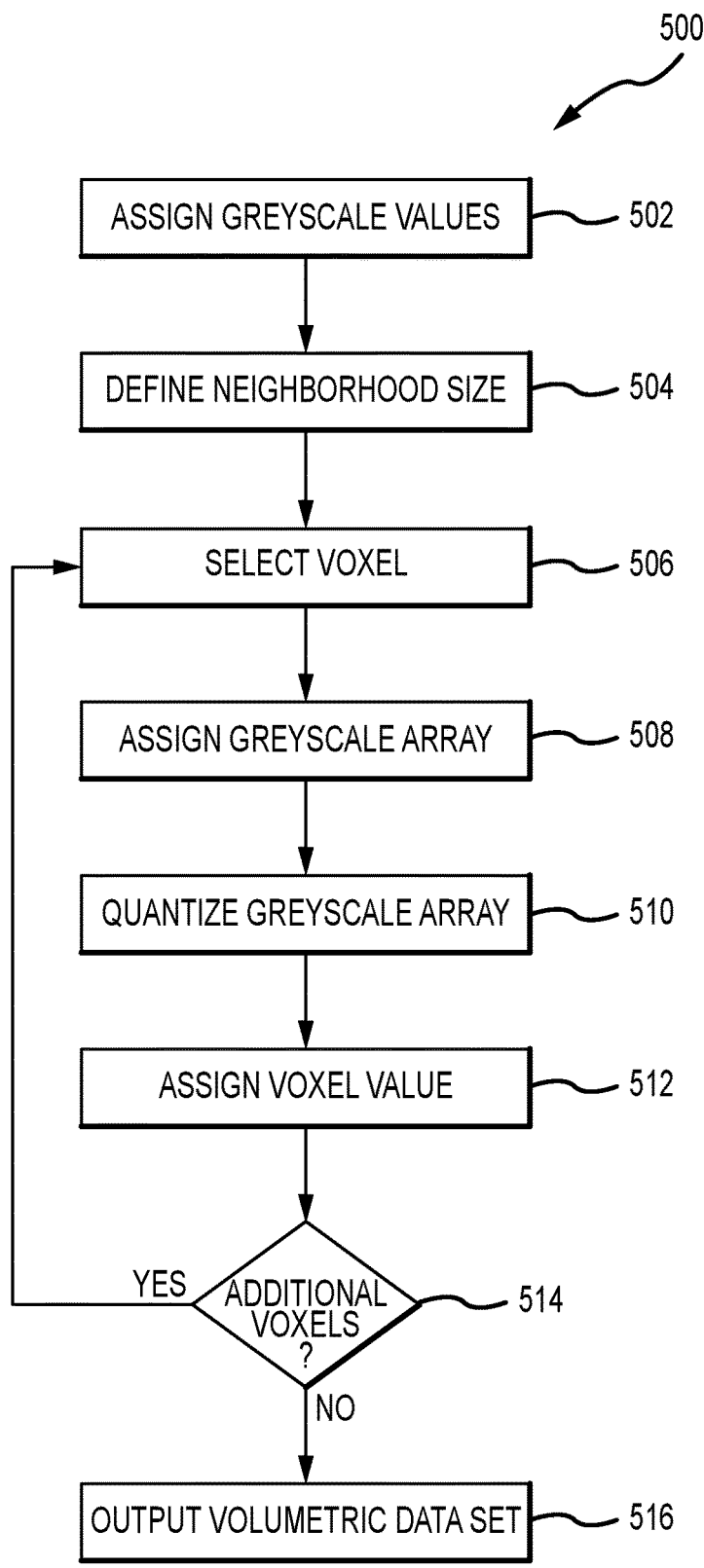
FIG. 5 is a flowchart of representative steps that can be followed when creating a volumetric data set according to exemplary embodiments of the present disclosure.

Once the filtered image slices are arranged into the voxel space, each voxel can be assigned a voxel value in block 310, thereby creating a volumetric data set. One suitable approach to assigning voxel values will be described with reference to flowchart 500 of FIG. 5.

In block 502, each voxel within the voxel space is assigned a greyscale value. A neighborhood size is defined in block 504.

A voxel is selected for processing in block 506. In block 508, the selected voxel is assigned a greyscale array, where the values in the array are defined by the respective greyscale values of neighboring voxels that are within the neighborhood size of the selected voxel.

Figure 6B:
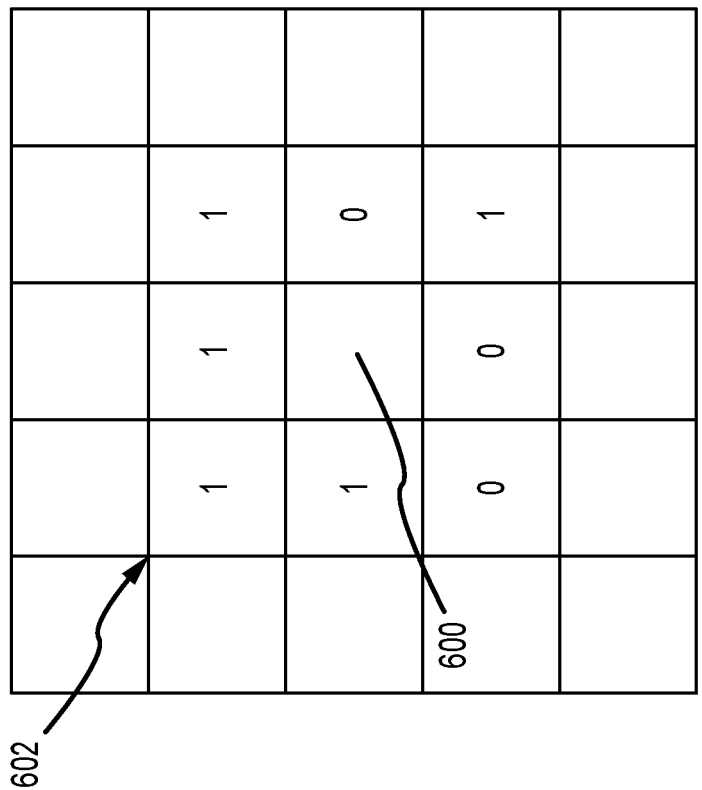
FIG. 6B illustrates a quantized greyscale array for a selected voxel as described herein.
Figure 6A:
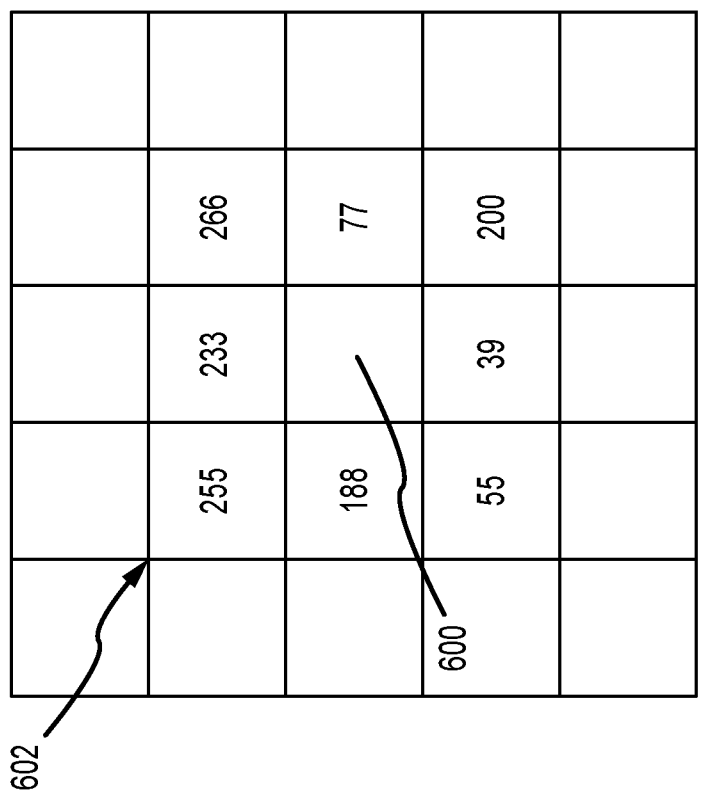
FIG. 6A illustrates a greyscale array for a selected voxel as described herein.

To aid in understanding, the process of assigning a greyscale array to a selected voxel is shown in two-dimensions in FIG. 6A. In particular, FIG. 6 depicts a selected voxel 600. Selected voxel 600 is surrounded by eight neighboring voxels 602 within a neighborhood size of one. Each neighboring voxel 602 is annotated with its greyscale value. Thus, the greyscale array for selected voxel 600 is [255, 233, 266, 77, 200, 39, 55, 188].

In block 510, the greyscale array is quantized into a preset number of buckets. The preset number of buckets can be user-defined. In aspects of the disclosure, the greyscale array is quantized into two buckets (e.g., "0" and "1"), thereby facilitating differentiation between tissue and blood pool. To aid in understanding, this is shown in FIG. 6B, where greyscale values over 150 are quantized into bucket "1" and greyscale values below 150 are quantized into bucket "0." Thus, the quantized greyscale array for selected voxel 600 is [1, 1, 1, 0, 1, 0, 0, 1].

In block 512, the selected voxel is assigned its voxel value according to the quantized greyscale array. For instance, the voxel value can be assigned according to majority vote of the quantized greyscale array; the voxel value of selected voxel 600, therefore, is 1, because the quantized greyscale array contains 5 instances of value "1" and 3 instances of value "0."

Decision block 514 considers whether there are additional voxels to process. If so (the "YES" exit from decision block 514), the process returns to block 506 for selection of a new voxel. If not (the "NO" exit from decision block 514), then a volumetric data set is output in block 516.

Thus, the volumetric data set includes a plurality of voxel values v(i, j, k), where i, j, and k are integer voxel indices such that $0 \leq i < N_x$, $0 \leq j < N_y$, and $0 \leq k < N_z$ ($N_x$, $N_y$, and $N_z$ are, respectively, the number of voxels in the x, y, and z directions). The practitioner can also define a range of voxel values between $v_{min}$ and $v_{max}$ if desired, such that only voxels within this range are rendered as described below.

In block 312, system 8 (e.g., module 58) renders a three-dimensional volumetric image from the volumetric data set. As used herein, the term "render" means to directly visualize the volumetric data, such as on display 23.

In general, the volumetric image can be rendered by dividing the voxel space into a plurality of parallel slices that are perpendicular to a preset viewing direction and alpha-blending the plurality of slices. The spacing between slices can be equal to the distance between a single voxel's two extreme corners in the preset viewing direction. It can also be desirable to render the slices from a most distant slice to a least distant slice, as determined relative to the preset viewing direction.

In aspects of the disclosure, the Open Graphics Library (OpenGL) application programming interface (API), and, in particular, OpenGL shaders, are used to render the volumetric image. Insofar as the use of the OpenGL API and alpha-blending will be familiar to those of ordinary skill in the art, they need only be described herein to the extent necessary to understand the instant disclosure.

In embodiments, the density gradient vector $\vec{g}(i, j, k)$ at a given voxel (i, j, k) is used to compute fragment colors and alpha values for the OpenGL rendering process. More specifically, the magnitude of the density gradient vector can be used to assign an alpha value, while the direction of the density gradient vector can be used for shading (that is, fragment color) purposes.

According to aspects disclosed herein, the gradient vector's x, y, and z components can be calculated by numerical differences in the relevant direction (e.g., via central-differencing, except at the boundaries of the volumetric data set, where forward- or backward-differencing is more appropriate).

By way of illustration, the gradient vector's x-component at voxel (i, j, k) can be computed as $$g_x(i, j, k) = \begin{cases} v_n(1, j, k) - v_n(0, j, k), i = 0; \\ \frac{1}{2}(v_n(i+1, j, k) - v_n(i-1, j, k)), 1 \leq i \leq N_x - 2; \\ v_n(N_x - 1, j, k) - v_n(N_x - 2, j, k), i = N_x - 1 \end{cases}$$

where $v_n$ is a voxel value normalized to $v_{min}$ and $v_{max}$ (that is, $v_n(i, j, k) = \max\{0, \min\{1, \frac{v(i, j, k) - v_{min}}{v_{max} - v_{min}}\}\}$).

Analogous equations can be used to determine the y and z components of the gradient vector at a given voxel (i, j, k).

As discussed above, the magnitude $\|\vec{g}\|$ of the gradient vector $\vec{g}(i, j, k)$ at voxel (i, j, k) can be used to compute an alpha value for voxel (i, j, k). In embodiments of the disclosure, the magnitude is first normalized by dividing it by its maximum possible value (e.g., $\sqrt{3}$). The practitioner can also select an opacity bias b, which ranges from −1 (fully transparent) to 1 (fully opaque). Because visual results may be too transparent for smaller biases, however, it is contemplated that a scaled opacity bias b' can be computed from the user-selected opacity bias b as $$b' = \frac{(3b + 1)}{4},$$

which will range between −0.5 and 1. The alpha value can be computed by exponentiating the normalized magnitude (e.g., $$\frac{\|\vec{g}\|}{\sqrt{3}})$$

by a function of the scaled opacity bias b', namely, $$\frac{2}{(b'+1)} - 1.$$

Similarly, the direction $\hat{g}$ of the gradient vector $\vec{g}(i, j, k)$ at voxel (i, j, k) can be used as the surface normal vector in the OpenGL shading equation, which computes fragment color based on material and light properties.

Color for OpenGL shading can be varied gradually, e.g., between blue at the most distant slice from the viewer and orange-brown at the least distant slice from the viewer, to provide a visual depth cue.

An initial step of the rendering process can find the range of slices that contain voxel values in the range of interest (e.g., between $v_{min}$ and $v_{max}$). This range of slices can be found quickly using an OpenGL shader. It can be used both to reduce the number of slices that are actually rendered, and to set the range of slices over which the depth-cueing color is varied.

Figure 7:
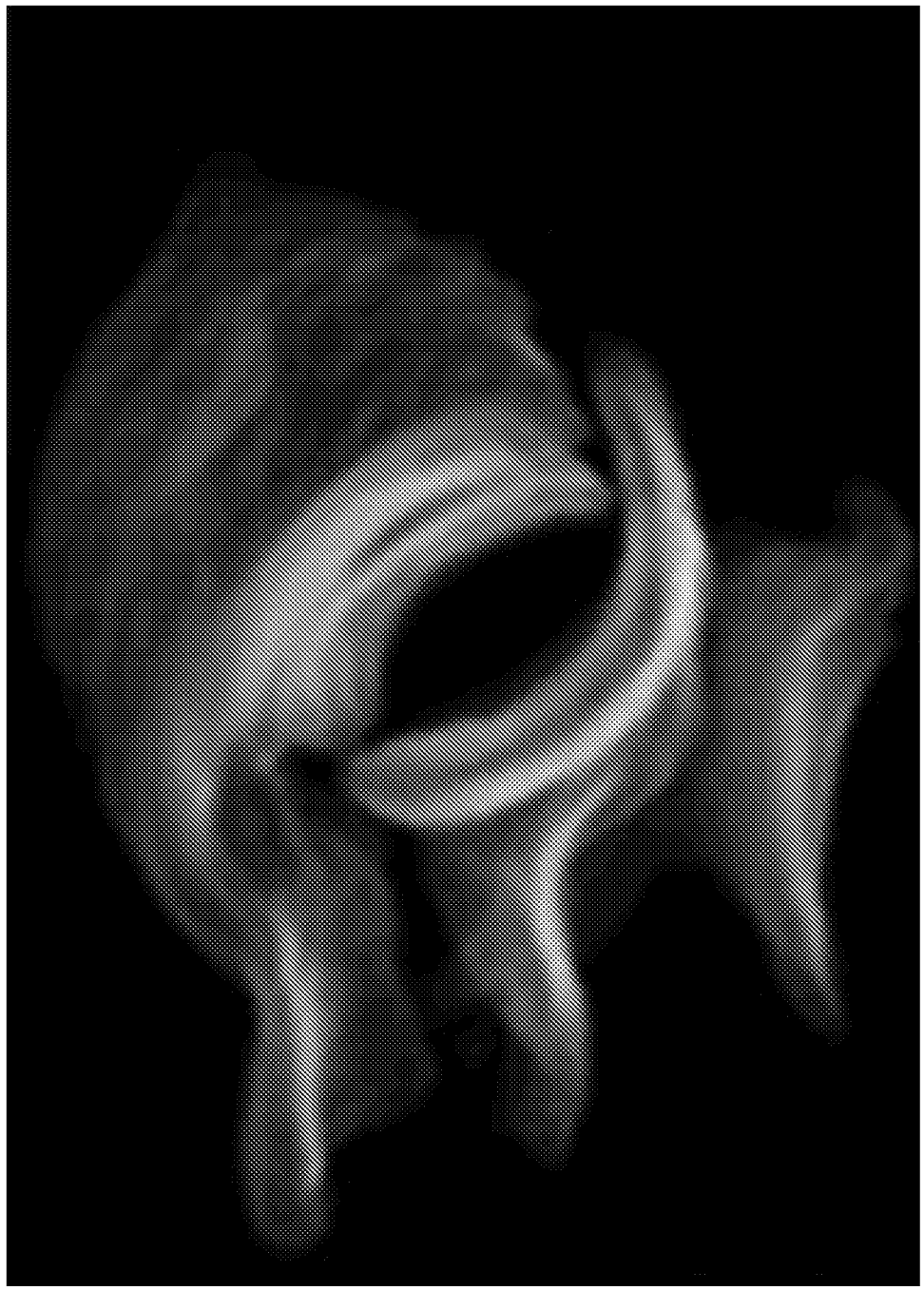
FIG. 7 depicts a representative three-dimensional volumetric image created according to embodiments of the instant disclosure.

FIG. 7 depicts a representative three-dimensional volumetric image 700 of a left atrium and two pulmonary veins according to the foregoing teachings.

Application of the foregoing teachings advantageously results in a three-dimensional volumetric image that accentuates the transition between regions of low- and high-density (e.g., blood-to-tissue boundaries. This is so even if the transition is smeared over several voxels due, for example, to ultrasound image fuzziness or imperfect gating. Indeed, as discussed above, the teachings herein can be applied to good advantage even to non-gated two-dimensional image slices.

Although several embodiments have been described above with a certain degree of particularity, those skilled in the art could make numerous alterations to the disclosed embodiments without departing from the spirit or scope of this invention.

For example, the teachings herein can be applied in real time (e.g., during an electrophysiology study) or during post-processing (e.g., to imagery collected during an electrophysiology study performed at an earlier time).

As another example, the filtering methodology described above in connection with two-dimensional image slices can also be applied to three-dimensional images.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of generating a three-dimensional image of an anatomical region from a plurality of two-dimensional echographic image slices of the anatomical region, wherein each image slice of the plurality of image slices is associated with localization information, the method comprising:
defining a three-dimensional voxel space comprising a plurality of voxels;
filtering the plurality of image slices using a reaction-diffusion partial differential equation model;
arranging the filtered plurality of image slices into the voxel space using the associated localization information;
assigning each voxel of the plurality of voxels a voxel value using the arranged, filtered plurality of image slices, thereby creating a volumetric data set; and
rendering a three-dimensional volumetric image from the three-dimensional data set, wherein the rendering comprises:
dividing the voxel space into a plurality of slices perpendicular to a preset viewing direction; and
alpha-blending the plurality of slices according to a process comprising, for each voxel within the plurality of voxels:
computing a density gradient vector;
computing a magnitude of the density gradient vector; and
assigning an alpha value using the magnitude of the density gradient value according to a process comprising:
normalizing the magnitude of the density gradient vector; and
exponentiating the normalized magnitude of the density gradient vector by an opacity bias.

2. The method according to claim 1, wherein assigning each voxel of the plurality of voxels a voxel value using the arranged, filtered plurality of image slices comprises:
assigning each voxel of the plurality of voxels a greyscale value;
defining a neighborhood size; and, for each voxel within the plurality of voxels:
assigning the voxel a greyscale array, wherein the greyscale array is defined by the respective greyscale values of a neighborhood of the plurality of voxels within the neighborhood size of the voxel;
quantizing the greyscale array to a preset number of buckets; and
assigning the voxel value to the voxel according to the quantized greyscale array.

3. The method according to claim 2, wherein assigning the voxel value to the voxel according to the quantized voxel array comprise assigning the voxel value to the voxel according to a majority vote of the quantized voxel array.

4. The method according to claim 1, wherein filtering the plurality of image slices using a reaction-diffusion partial differential equation model comprises filtering the plurality of image slices using an Allen-Cahn-type reaction-diffusion model.

5. The method according to claim 1, wherein dividing the voxel space into a plurality of slices perpendicular to a preset viewing direction occurs from a most distant slice of the plurality of slices to a nearest slice of the plurality of slices, as determined relative to the preset viewing direction.

6. The method according to claim 1, wherein the opacity bias comprises a user preset value.

7. The method according to claim 1, wherein the opacity bias comprises a scaled opacity bias.

8. The method according to claim 1, wherein rendering the three-dimensional volumetric image from the three-dimensional data set further comprises, for each voxel within the plurality of voxels:
  computing a density gradient vector;
  computing a direction of the density gradient vector; and
  defining the direction of the density gradient vector as a surface normal vector for shading purposes.

9. A method of generating a three-dimensional geometric image of an anatomical region, the method comprising:
  defining a three-dimensional voxel space comprising a plurality of voxels;
  receiving a plurality of two-dimensional echographic image slices of the anatomical region, wherein each image slice of the plurality of image slices is associated with localization information;
  arranging the plurality of image slices into the voxel space using the associated localization information, thereby creating a volumetric data set; and
  rendering a three-dimensional volumetric image from the three-dimensional data set,
  wherein rendering the three-dimensional volumetric image from the three-dimensional data set comprises, for each voxel within the plurality of voxels:
    computing a density gradient vector;
    computing a magnitude of the density gradient vector; and
    assigning an alpha value for alpha-blending purposes using the magnitude of the density gradient vector, wherein the assigning comprises:
      normalizing the magnitude of the density gradient vector; and
      exponentiating the normalized magnitude of the density gradient vector by an opacity bias.

10. The method according to claim 9, wherein the opacity bias comprises a user preset value.

11. The method according to claim 9, wherein the opacity bias comprises a scaled opacity bias.

12. The method according to claim 9, wherein rendering the three-dimensional volumetric image from the three-dimensional data set further comprises:
  computing a direction of the density gradient vector; and
  defining the direction of the density gradient vector as a surface normal vector for shading purposes.

13. The method according to claim 9, further comprising, prior to arranging the plurality of image slices into the voxel space using the associated localization information, thereby creating the volumetric data set, filtering the plurality of image slices using a reaction-diffusion partial differential equation model.

14. The method according to claim 13, wherein the reaction-diffusion partial differential equation model comprises an Allen-Cahn-type reaction-diffusion model.

15. The method according to claim 9, wherein arranging the plurality of image slices into the voxel space using the associated localization information, thereby creating the volumetric data set, comprises, for each voxel of the plurality of voxels:
  assigning the voxel a greyscale value;
  defining a neighborhood size;
  assigning the voxel a greyscale array, wherein the greyscale array is defined by the respective greyscale values of a neighborhood of the plurality of voxels within the neighborhood size of the voxel;
  quantizing the greyscale array to a preset number of buckets; and
  assigning a final voxel value to the voxel according to the quantized greyscale array.

16. A system for generating a three-dimensional geometric image of an anatomical region, comprising:
  an imaging and modeling module configured to:
    define a three-dimensional voxel space comprising a plurality of voxels;
    receive a plurality of two-dimensional echographic image slices of the anatomical region, wherein each image slice of the plurality of image slices is associated with localization information;
    arrange the plurality of image slices into the voxel space using the associated localization information, thereby creating a volumetric data set;
    compute a density gradient vector for each voxel within the plurality of voxels; and
    render a three-dimensional volumetric image from the three-dimensional data set using a magnitude of the density gradient vector to assign an alpha value for alpha-blending purposes and a direction of the density gradient vector as a surface normal vector for shading purposes, wherein using the magnitude of the density gradient value to assign the alpha value comprises:
      normalizing the magnitude of the density gradient vector; and
      exponentiating the normalized magnitude of the density gradient vector by an opacity bias.

* * * * *